United States Patent [19]

Hideshima et al.

[11] Patent Number: 5,374,967
[45] Date of Patent: * Dec. 20, 1994

[54] OPHTHALMOLOGICAL IMAGE PROCESSING SYSTEM

[75] Inventors: Masayuki Hideshima; Toru Suzuki; Akio Sakurai; Yoshio Okazaki; Akio Morimoto, all of Tokyo, Japan

[73] Assignee: Kabushiki Kaisha Topcon, Tokyo, Japan

[*] Notice: The portion of the term of this patent subsequent to Mar. 1, 2011 has been disclaimed.

[21] Appl. No.: 104,900

[22] Filed: Aug. 12, 1993

Related U.S. Application Data

[63] Continuation of Ser. No. 800,619, Nov. 27, 1991, Pat. No. 5,291,231.

[30] Foreign Application Priority Data

Nov. 29, 1990 [JP] Japan ................................. 2-331279

[51] Int. Cl.⁵ .............................................. A61B 3/14
[52] U.S. Cl. .................................. 351/208; 351/206; 354/62

[58] Field of Search ............... 351/208, 206, 207, 205; 354/62

[56] References Cited

U.S. PATENT DOCUMENTS

5,118,179  6/1992  Sano et al. ............................. 351/206
5,291,231  3/1994  Hideshima et al. .................. 351/206

Primary Examiner—William L. Sikes
Assistant Examiner—Hung Xuan Dang
Attorney, Agent, or Firm—Finnegan, Henderson, Farabow, Garrett & Dunner

[57] ABSTRACT

This invention provides an ophthalmological image processing system which can avoid data errors when processing images by appending data to identify a subject's left and right eyes, and other photographic condition data. The system comprises an ophthalmological camera for electronically obtaining an image of a subject's eyes, inputting means for inputting photographic condition data, and processing means for linking a fundus image obtained by the ophthalmological camera to the photographic condition data input by the inputting means.

4 Claims, 5 Drawing Sheets

OPHTHALMOLOGICAL IMAGE PROCESSING SYSTEM

This is a continuation of application Ser. No. 07/800,619, filed Nov. 27, 1991, now U.S. Pat. No. 5,291,231.

BACKGROUND OF THE INVENTION

1. Field of the Invention

This invention concerns an ophthalmological image processing system for electronic filing of ophthalmological images such as may be obtained by ophthalmological cameras in particular images of the fundus or front chamber of a subject's eye, or for transferring data between an ophthalmological camera and an image analyzer (data processor).

2. Description of the Prior Art

In recent years, there has been a tendency to replace photographs taken on silver halide film by electronic images. This is true not only in the ophthalmological field, but also where electronic images offer particular advantages such as in periodic health check-ups or for examining the three-dimensional structure of a fundus. Electronic images are thus making progressive inroads, initially in those fields where it would be difficult to perform the task at hand without them.

To make effective use of electronic filing, the following subject data must be input in the form of search codes:

(1) Name
(2) Sex
(3) Age
(4) Present address
(5) Previous address
(6) Examination date In addition, in the ophthalmological fields, it is also required to input information regarding (7) the difference between the left and right eyes.

In the case of items (1)–(5), once the information is input it can be used any number of times, and in many cases it can be accessed by known techniques via a network from a hospital or health center data base. Further, if a clock function is built into the filing system, it can be input automatically by known techniques.

One example of the aforesaid ophthalmological camera is that of a fundus camera which makes observations and takes photographs of, for example, retinal blood vessels in the fundus or optic nerve papillae of a subject's eye. The size, shape and other characteristics of the blood vessels or papillas can be analyzed by this fundus camera in order to determine whether or not the fundus has a disorder, or the nature of such a disorder if present.

In recent years, in this type of ophthalmological camera, systems have been developed to permit magnetic recording and storage of photographed images on a magnetic support. In such a camera, information such as viewing angle, amount of light and filters used, etc., can also be entered from a keyboard or other input means before taking a photograph.

Methods are also being proposed to perform more detailed analyses of the images recorded on the support, and display the results of processing on a monitor TV or print them out.

This analysis also requires knowledge of the conditions existing when the photograph was taken such as viewing angle, amount of light and filters used.

However, the electronic image inputting apparatus often consisted merely of a conventional silver halide fundus camera or slit lamp to which an adapter had been added, and the information had to be input manually each time a photograph was taken. This placed a nervous strain on the operator who already had sufficient work to do to input the image, often causing the operator to forget to specify the left or right eye or to confuse them.

Further, when the aforesaid fundus camera was used in conjuction with an image analyzer, information regarding photographic conditions was input to the analyzer based on but separate from the information input to the camera, and this required more effort.

Input of information regarding photographic conditions to the analyzer was moreover based on the operator's notes or memory, and occasionally led to errors.

SUMMARY OF THE INVENTION

It is therefore an object of this invention to provide an ophthalmological image processing system wherein left/right eye identification data and other information can automatically be added to image data when image recordings are made, thereby avoiding nervous strain on the operator and data input errors.

To achieve this object, the invention of claim 1 is characterized by an opthalmological camera for electronically obtaining an image of a subject's eye, inputting means for inputting photographic condition data, and data processing means for linking the image obtained by this ophtalmological camera to the photographic condition data input by this data inputting means.

It is a further object of this invention to provide an opthalmological image processing system wherein the inputting of photographic condition data to an image analyzer and an ophthalmological camera is facile and involves no errors.

The invention of claim 7 is characterized in that the data processing means is connected to the ophthalmological camera, and either the data processing means or camera comprises, or both comprise, a means for linking photographic condition data input by the inputting means to left/right eye identfication data, and transferring it to the other apparatus.

These and other objects, features and advantanges of the present invention will be well appreciated upon reading of the following description of the invention when taken in conjunction with the attached drawings with understanding that some modifications, variations and changes of the same could be made by the skilled person in the art to which the invention pertains without departing from the spirit of the invention or the scope of the claims appended thereto.

DESCRIPTION OF THE PREFFERRED EMBODIMENT

This invention will now be described with reference to the drawings.

(Embodiment 1)

Figure 1:
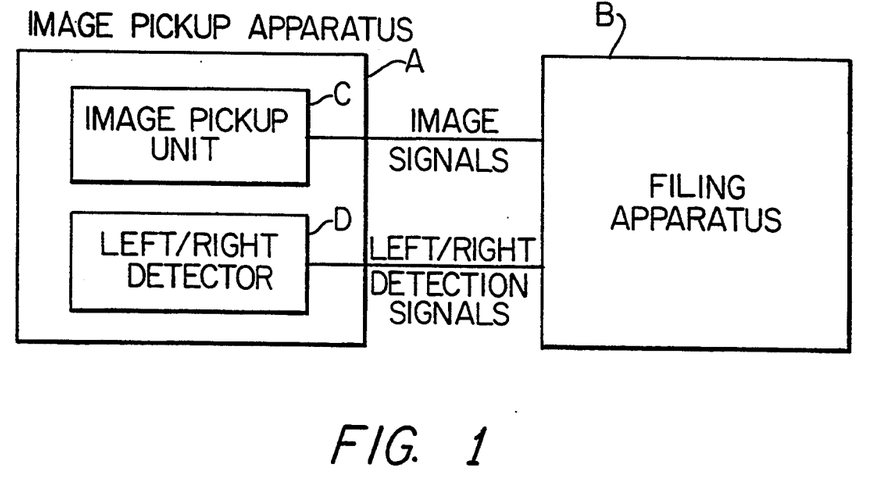
FIG. 1 is a block diagram illustrating a first embodiment of the ophthalmological image processing system of this invention.

FIG. 1 shows a basic block diagram of the ophthalmological filing system of this invention.

This filing system broadly comprises an image pickup apparatus A for photographing electronic images, and a filing apparatus B. The pickup apparatus A contains of an ordinary slit lamp or fundus camera. Further, the filing apparatus B (data processing means) comprises a recording means consisting of a high capacity recording device such as an image memory, magnetic disk, optical disk or magneto-optic disk and circuits to control these devices. The image pickup apparatus A has an image pickup unit C which picks up for example a fundus image and a detector D which identifies left and right (photographic condition input means), the signals output by the image pickup unit C and the detector D being input to the filing apparatus. Inputting of electronic images is performed with a specified timing by a trigger switch, not shown.

In the following description, the image pickup apparatus and the filing apparatus are treated separately, but in practice they can form a one-piece construction.

Figure 2:
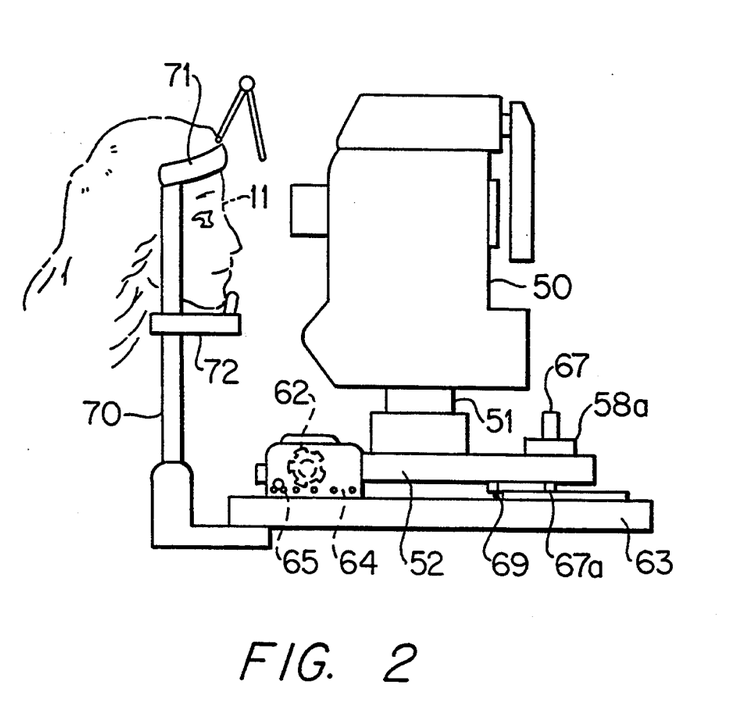
FIG. 2 is an oblique view of a fundus camera illustrating one example of the image pickup apparatus of FIG. 1.
Figure 3:
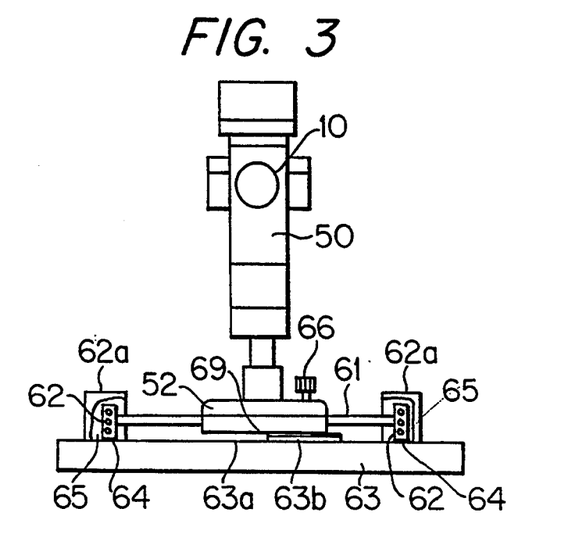
FIG. 3 is a front view of the fundus camera of FIG. 2.

FIGS. 2 and 3 illustrate a fundus camera as an example of one type of image pickup apparatus.

Image pickup devices such as an illuminating light source, illuminating optical system, observation/photographic optical system, ordinary camera tube or CCD (charge coupling device) and the image pickup unit comprising circuits for driving these devices and processing their signal outputs), are housed in a chassis 50.

Figure 4:
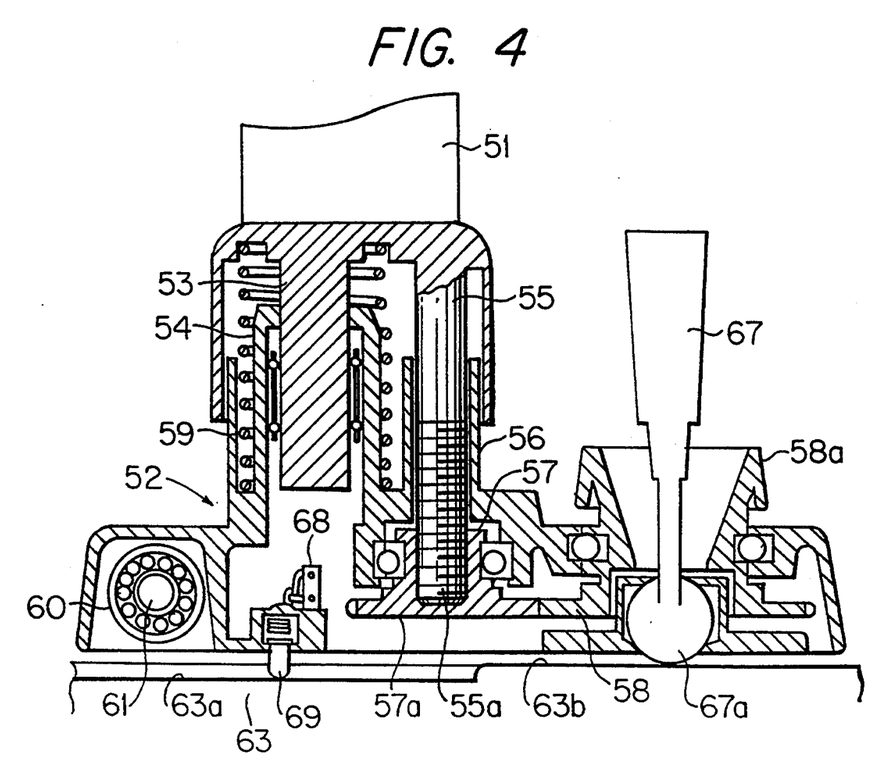
FIG. 4 is a sectional view showing the left/right moving mechanism of FIG. 2.

The chassis 50 is provided with a support 51 projecting downwards of which the lower end is supported by a platform 52 that can be moved back and forth. The chassis 50 is also provided with a guide rod 53 which extends downwards, and a guide tube 54 being formed in the platform 52 for guiding the rod 53, so as to prevent rotating the screw rod 55 and permit adjusting the vertical position of the chassis, as shown in FIG. 4.

Further, a screw rod 55 extends downwards on the support 51, and passes through a cylindrical guide 58 in the platform 52. A male screw member 55a is formed in the lower part of the screw rod 55, this member 55a engaging with a nut 57 supported on the platform 52 such that the nut is free to rotate.

An toothed gear 57a is formed on the nut 57. This gear 57a engaging with a toothed gear 58 supported on the platform 52 such that the gear 58 is free to rotate. This gear 58 is formed in a one-piece construction with a control ring 58a projecting upwards from the platform 52. By manipulating the control ring 58a, the support 51 and therefore the chassis 50 can be moved up and down.

A coil spring 59 is wound around the guide tube such that it acts between the lower edge of the support 51 and the platform 52, and supports the weight of the image pickup apparatus.

A bearing 60 is disposed at the front of the platform 52, and a horizontal guide rod 61 is inserted in this bearing 60 such that the rod is free to slide and rotate. As shown in FIG. 3, wheels 62 are attached to both ends of the guide rod 61, these wheels 62 being disposed so as to follow tracks 64 on a table 63. A plurality of pins 65 are fixed on the tracks 64 at equidistant intervals, holes 62a being formed on the circumferential surface of the wheels 62 so as to engage with these pins 65.

Due to the engaging of the holes 62a of the wheels 62 and the pins 65, the wheels 62 are constrained to follow the track 64. The rod 61 is free to slide in an axial direction with respect to the bearing 60, therefore the platform 52 can be moved horizontally along the guide rod 61. A locking mechanism, not shown, is provided for fixing the platform 52 on the guide rod 61, this locking mechanism being applied by a control knob 66 shown in FIG. 3.

A plane surface 63b on the left hand side is formed one level higher than a plane surface 63a on the right hand side of the apparatus as viewed from an objective lens 10 of the table 63. At the rear of the platform 52, a spherical member 67a at the front end of a joystick 67 is supported such that it is free to rotate so as to control the front, back, left and right movement of the apparatus.

In the platform 52, there is provided a microswitch 68 as a left/right detector (photographic condition inputting means), and a pin 69 to activate this microswitch 68. This pin 69 projects downwards from the platform 52. A forehead support 71 and a chin support 72 are supported in front of the table 63 by a support 70, and the position of the chassis 50 is fixed such that the objective lens 10 faces the subject's eye 11.

To take a photograph of the subject's right eye, the chassis 50 supported on the platform 52 is moved to the left as viewed from the subject by means of the stick 67. The switching pin 69 then moves onto the plane 63b which is one level higher than the plane 63a of the table 63 so as to cause the switch 68 to operate.

The signal from this switch 68 for detecting left and right is input to the filing apparatus (FIG. 1).

The filing apparatus B is so arranged that data for identifying left and right photographic images according to the output of the switch 68 can be added for the purpose of electronic filing when taking a photograph. The filing system is so arranged such that any of the following filing methods, or any combination of them, can be performed instead of manual input by referring to the left/right detection signal from the switch 68 when an image is input:

(1) Adding a mark for identifying the left and right eyes to the image data, (2) Adding a file name according to whether an image corresponds to the left or right eye, (3) Selecting a storage position for image data.

It is necessary only to move the chassis of the image pickup apparatus to the left or right when photographing the left or right eye of the subject. By means of this action the apparatus identifies the eye to which the image corresponds, and when the electronic image is filed the required operations are carried out automatically.

Figure 5:
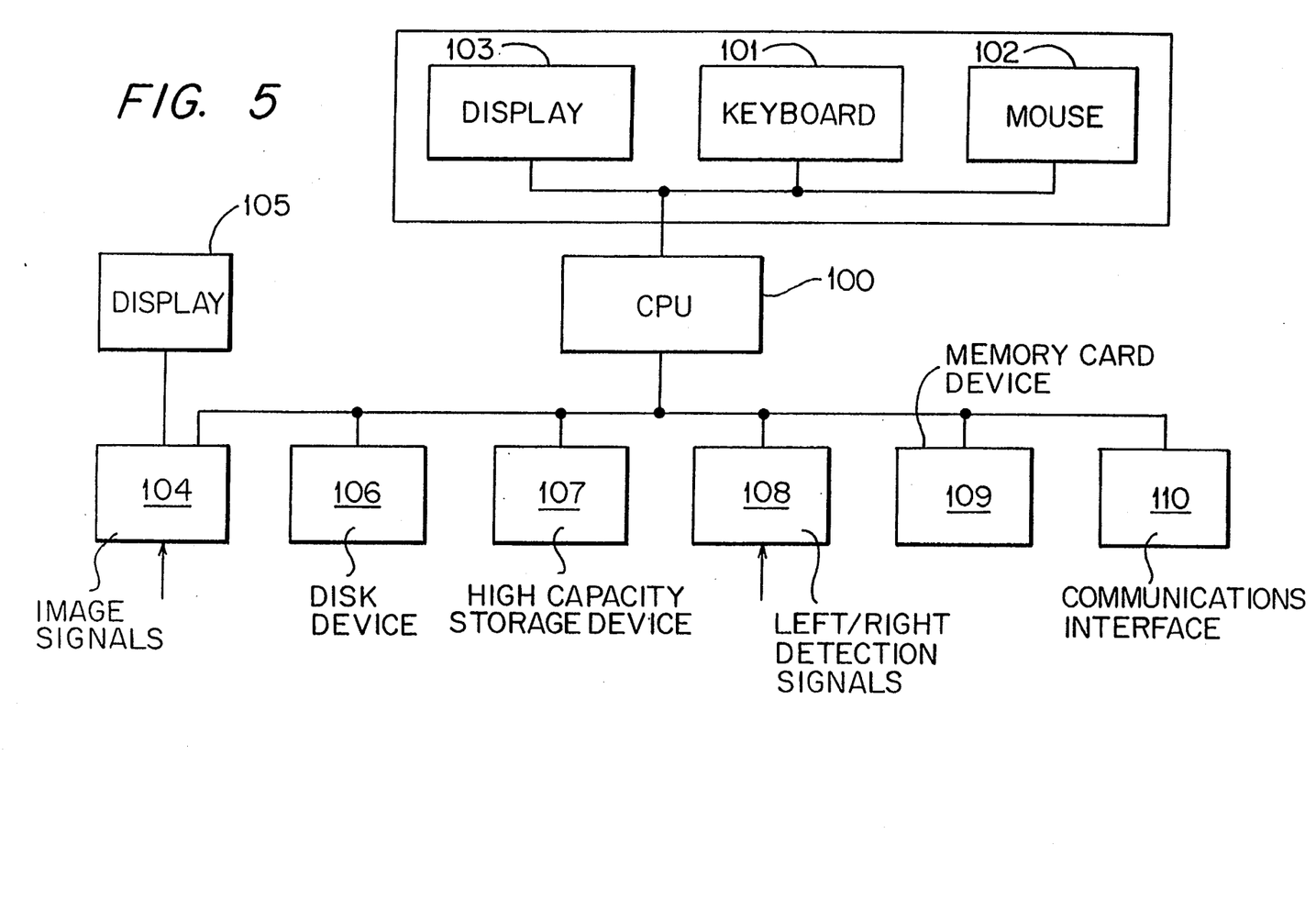
FIG. 5 is a block diagram illustrating an ophthalmological image filling system of this invention.

FIG. 5 shows a typical block diagram of an ophthalmological image filing system according to this invention.

This image filing system comprises a central processing unit (CPU) 100 for creating a data base, managing image files and processing images which is provided with a control terminal consisting of a keyboard 101, mouse 102 (pointing device) and display 103.

The filing system also comprises an image memory 104 for temporary storage of input image signals, an image display 105 for displaying image data stored in the image memory 104, and a disk device 106 for storing programs of the CPU 100 or temporary image data by means of magnetic recording.

Further, the filing system also comprises a high capacity storage device 107 consisting of for example a optical or magneto-optic disk for permanent storage of image data or creating a database (write once optical disk or read/write magneto-optic disk). Further, the filing system also comprises a universal interface 108 for input/output of left/right detection signals or an image pickup timing signal, not shown, a memory card device 109 for read/write memory cards used to transfer small amounts of image data or data bases, and a communications interface 110 for communicating with external equipment.

Image data is stored in the image memory 104 and displayed on the image display 105. From this display, the operator can decide whether or not an image data is suitable for filing. If he decides that it is suitable, the data is input through the communications interface 110, input through the keyboard 101 or integrated in a data base with subject data obtained previously for storing by the high capacity storage device 107 consisting of an optical disk or magneto-optic disk.

The subject's name or ID number is added to the image data, and is stored in the high capacity storage device 107 at the same time as photographic condition data (e.g. left or right eye, photography by fluorescence, amount of light and magnification) input from a left/right identification apparatus, keyboard 101 and other peripheral devices. This constitutes a data base from which image data or photographic conditions can be recalled.

If a plurality of images of the same subject are taken and only specific images are to be filed, the data may also be temporarily stored in the disk device 106. Recording supports such as optical disks or magneto-optic disks are interchangeable, and image data for at least 100 people can be stored on one support. In group health check-ups, therefore, one recording support would be sufficient for one day's work, and the data could also be transferred to health centers and photographic locations.

Further in hospitals, when it is required to transfer only a very small amount of image data required for a single examination of one patient, the use of a high capacity storage device is unnecessary. In such a case, a memory card of suitable capacity or a magnetic recording means such as a magnetic disk (floppy disk) may be used as a recording support.

The image data is filed by means of a CPU program stored in the disk device 106. In this case, personal information about the subject and image data could be linked or cross-referenced by the following methods:
(1) Editing and storing personal data and image data in the same file. (2) Storing personal data and image data in completely different files,
(3) Saving only a personal data file in the data base, the image data file name being specified in the personal data file.

The left and right eyes must be distinguished from one another for retrieval at a later date. This could be accomplished in each of the above methods as follows:
Method (1):
Data could be listed in the order:
Personal data, left eye, right eye.
Method (2):
Data identifying the left eye and right eye could be attached to the file name.
Method (3):
A correspondance table for the left eye, right eye and image file could be constructed in the personal data file.

This filing apparatus B and controlling software is easily implemented by a personal computer, hardware options and data base software. Data can also be input manually from a keyboard.

Further, the high capacity storage device 107 may consist of a first recording device, and the disk apparatus 106 may consist of a second recording device. The ophthalmological image is then recorded on the first recording device (magneto-optic disk) together with identifying data, and photographic condition data is recorded on the second recording device (floppy disk) together with the same identifying data.

(Embodiment 2)

Figure 6:
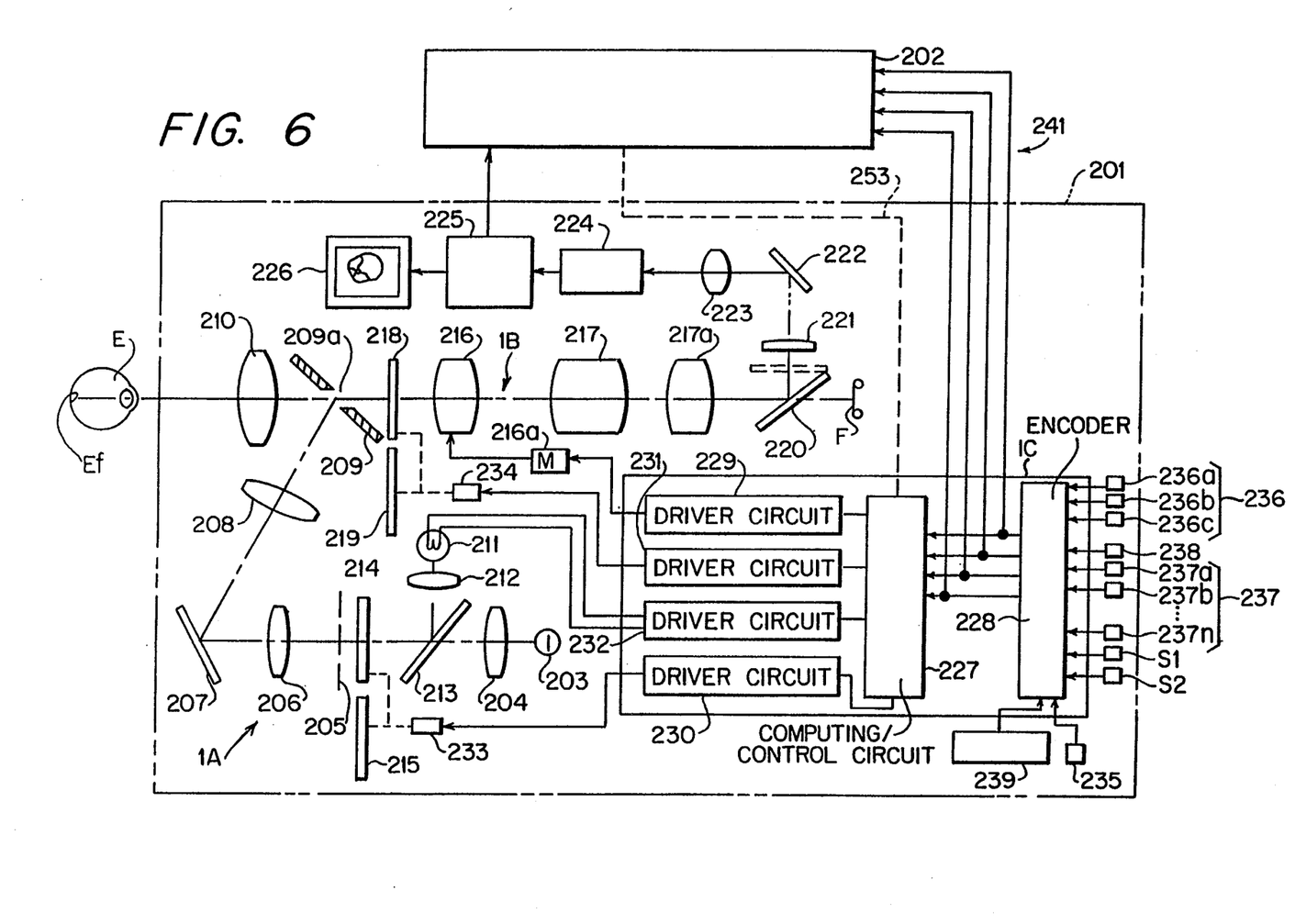
FIG. 6 is a schematic diagram illustrating a second embodiment of the ophthalmological image processing system of this invention.

In FIG. 6, the ophthalmological image processing system of this invention comprises an ophthalmological camera 201 and an image analyzer 202 (data processing means) connected to this ophthalmological camera 201.

Ophthalmological Camera 201

The ophthalmological camera 201 comprises an illuminating optical system 1A, an observation/photography optical system 1B and a control circuit 1C. The illuminating optical system 1A comprises an illuminating system for observation and an illuminating system for photography.

The illuminating system for observation comprises optical components consisting of an observation light source 203, a condensing lens 204, ring slit 205, relay lens 206, reflecting mirror 207, relay lens 208, holed mirror 209 and objective lens 201 arranged in that order. Illuminating light from the optical source 203 passes through the condensing lens 204, ring slit 205, relay lens 206, reflecting mirror 207, relay lens 208, holed mirror 209 and objective lens 210 so as to illuminate a fundus Ef of the subject's eye E. 209a is a center hole of the holed mirror 209.

The illuminating system for photography comprises a photographic light source 211 such as a xenon lamp, condensing lens 212, half mirror 213 interposed between the condensing lens 204 and ring slit 205, and the optical components from the ring slit 205 to the objective lens 210 of the observation illuminating optical system. Illuminating light from the photographic light source 211 passes through the condensing lens 212, half mirror 213 interposed between the condensing lens 204 and ring slit 205, and the optical components from the ring slit 205 to the objective lens 210 of the observation illuminating optical system so as to illuminate the fundus Ef.

An exciter filter 214 (optical component) for photography by visible light-excited fluorescence and an exciter filter 215 (optical component) for photography by infrared light-excited fluorescence are disposed such they can be selectively interposed between this half mirror 213 and ring slit 205.

The observation/photography optical system 1B comprises a film-photography system and an observation system.

The film photography system comprises the objective lens 210, the holed mirror 209, a variable power lens 216, focusing lens 217 and imaging lens 217a. Light reflected from the fundus Ef passes through the objective lens 210, hole 209a of the holed mirror 209, variable lens 216, focusing lens 217 and imaging lens 217a to a 35 mm photographic film F. A still video camera may be installed in place of this 35 mm photographic film F.

A barrier filter 218 (optical component) for photography by visible light-excited fluorescence and a barrier filter 219 (optical component) for photography by infrared light-excited fluorescence are disposed such that they can be selectively interposed between this holed mirror 209 and variable power lens 216.

The observation system comprises the optical components from the objective lens 210 to the focusing lens 217 of the film photography optical system, and a quick return mirror 220, field lens 221, reflecting mirror 222 and relay lens 223. This quick return mirror 220 is disposed such that they can be selectively interposed between the imaging lens 217a and film F.

When the quick return mirror 220 is interposed between the focusing lens 217 and the film F, light reflected from the fundus guided to the imaging lens 217a passes through the quick return mirror 220, field mirror 221, reflecting mirror 222, relay lens 223 to the photographic device 224.

The signal output by this photographic device 224 is input to an image processing circuit 225. The image processing circuit 225 processes the signal output by the photographic device 224, and inputs a fundus image signal to a monitor TV 226. A fundus image is thereby displayed on the monitor TV 226.

A control circuit IC comprises a computing/control circuit 227, an encoder 228 (part of the transmission means) connected to the input side of this control circuit 227, driver circuits 229, 230, 231 and a light emission control circuit 232.

The computing/control circuit 227 controls the amount of light emitted by the photographic light source 211 via the light emission control circuit 232, and drives a motor 216a of the variable power lens 216 via the driver circuit 229.

The computing/control circuit 227 drives and controls a motor 233 which drives the exciter filters 214, 215 of the aforesaid optical system via the driver circuit 230, and selectively interposes the exciter filters 214, 215 in the optical path of the illuminating optical system 1A.

Further, the computing/control circuit 227 drives and controls a motor 234 which drives the barrier filters 218, 219 via the driver circuit 231, and selectively interposes the exciter filters 218, 219 in the optical path of the observation/photography optical system 1B.

Further, the exciter filters 214, 215 are respectively driven in synchronism with the barrier filters 218, 219.

A camera switch 235 for taking photographic, viewing angle setting means 236, light amount setting means 237, switch 238 to determine whether the left or right eye is being photographed, and a photographic mode selector switch S1 for selecting either photography on the 35 mm film F or still image photography by the photographic device 224, are connected to the encoder 228 for inputting photographic condition data. The viewing angle setting means 236 has switches 236a, 236b, 236c for setting the viewing angle to 20°, 35° and 50°, while the light amount setting means 237 has a plurality of switches 237a ... 237n for setting the light amount from 18 W to 300 W.

Each time the photographic mode selector switch S1 is pressed, photography on the 35 mm film F or still image photography by the photographic device 224 are alternately selected.

Further, a selector switch S2 is connected to the encoder 228 for selecting ordinary visible light photography (including color photography), photography by visible light-excited fluorescence or photography by infrared light-excited fluorescence (photographic condition data).

Further, a keyboard 239 (photographic condition inputting apparatus) for inputting identifying data such as the subject's name or ID number is connected to the computing/control circuit 227 through the encoder 228. This encoder 228 converts photographic condition data input by the keys and switches and data for identifying the subject's eyes into hexadecimal notation, and outputs corresponding data.

Next, the method of taking photographs on the 35 mm film F will be described using the aforesaid equipment arrangement, and using equipment arrangements other than the aforesaid arrangement.

To take a photograph on a 35 mm film F after observing a fundus image on the monitor TV 226, one of the viewing angle setting switches 236a, 236b, 236c is selected by turning it to the ON position. This ON signal is input to the computing control circuit 227 via the encoder 228. The computing/control circuit 227 drives a motor 216a via the driver circuit 229 so as to set the photographic viewing angle. The whole ophthalmological photographic apparatus 201 is then moved into a desired position for taking a photograph while viewing the fundus image on the monitor TV 226.

One of the switches 237a ... 237n for setting the amount of light is selected, 35 mm film photography is selected by the photographic mode switch S1, and the type of photography, i.e. ordinary visible light photography (including color photography), photography by visible light-excited fluorescence or photography by infrared light-excited fluorescence, is selected. The ON signals from these switches S1, S2, 37a ... 37n are input to the computing/control circuit 227 via the encoder 228.

When the camera switch 235 is pressed ON, this ON signal is input to the computing/control circuit 227 via the encoder 228. At the same time, the computing control circuit 227 causes the quick return mirror 214 to be removed from the optical path between the 35 mm film F and the focusing lens 217 by a drive means, not shown.

If photography by visible light-excited fluorescence is selected, the computing control circuit 227 drives the motor 233 via the driver circuit 230 so as to insert the exciter filter 214 in the illuminating optical path, and drives the motor 234 via the driver circuit 231 so as to insert the barrier filter 218 in the observation/photographic optical path.

If photography by infrared light-excited fluorescence is selected, the computing/control circuit 227 drives the motor 233 via the driver circuit 230 so as to insert the exciter filter 215 in the illuminating optical path, and drives the motor 234 via the driver circuit 231 so as to insert the barrier filter 219 in the observation/photographic optical path. Further, when taking ordinary photographs, the filters 214, 215, 218, 219 are removed from the optical path.

Next, the computing/control circuit 227 controls the light emitted by the photographic light source 211 via the light emission control circuit 232 based on information from the light amount setting means 237. The illuminating light from this photographic light source 211 passes through the condensing lens 212, half mirror 213, and illuminates the fundus Ef via the optical components from the ring slit 205 to the objective lens 210 of the illuminating optical system for observation. The light reflected from this fundus Ef is guided to the 35 mm photographic film F via the objective lens 210, center hole 209a of the holed mirror 209, variable power lens 216 and focusing lens 217 so that a fundus image is photographed on the 35 mm film F.

If a still video camera is used instead of this 35 mm film F. a fundus image signal is recorded on a video floppy of the still video camera. In this case, data for identifying the subject's eyes is also transferred from the computing control circuit 227 to the still video camera to be recorded on the video floppy.

Further, in the case of photography by fluorescence of the blood vessels in the fundus using angeography, a photograph of the fundus is taken at fixed time intervals. This time information is measured by a timer or other device, photographed by the 35 mm camera, and also recorded on the video floppy.

Image Analyzer 202

Next, the image analyzer 202 will be described.

Figure 7:
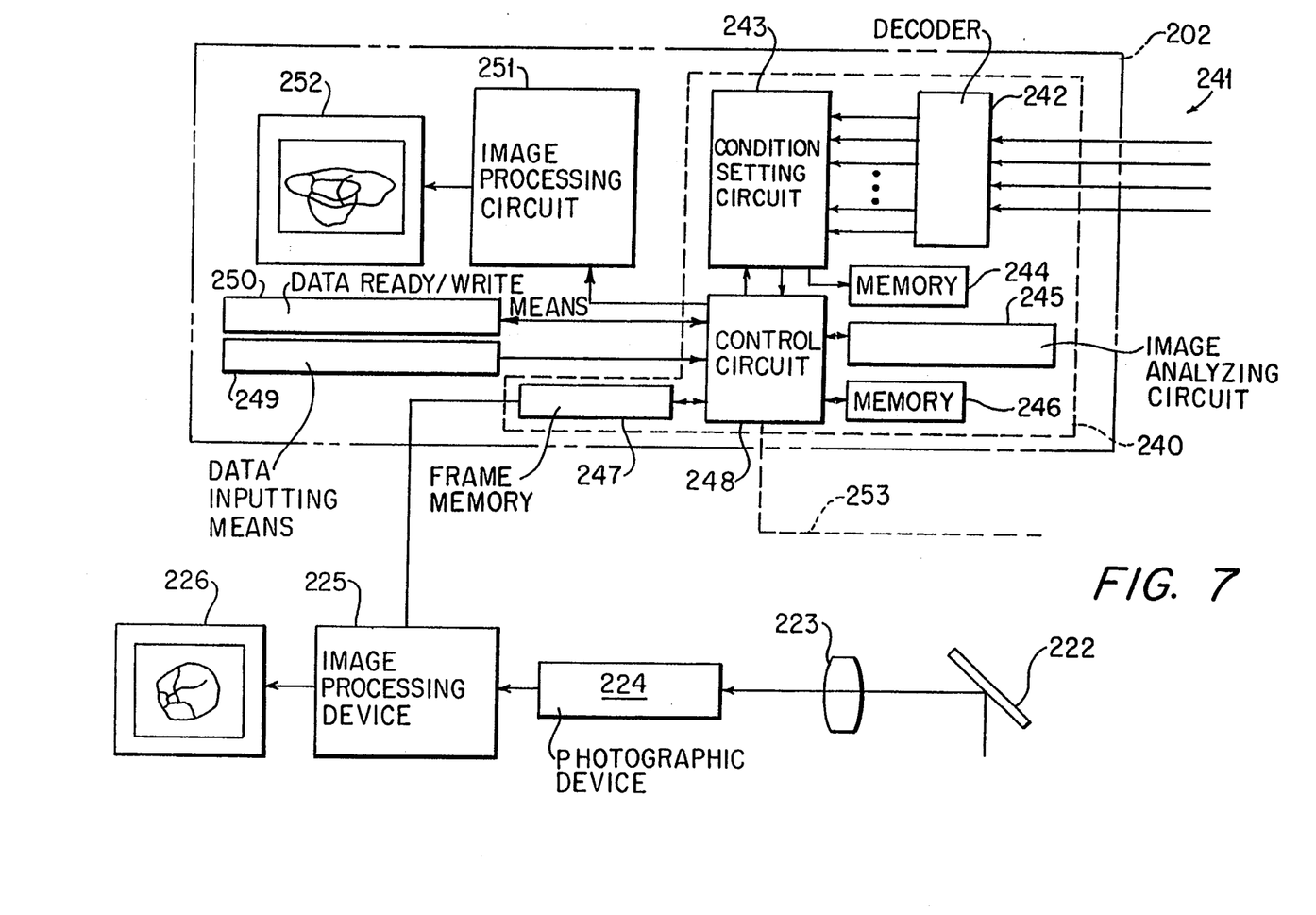
FIG. 7 is a detailed schematic diagram of the image analyzer shown in FIG. 6.

The image analyzer 202 comprises a computing/control circuit 240 as shown in FIG. 7. This computing-/control circuit 240 comprises a decoder 242 connected to the ophthalmological photographic apparatus 1 via a connecting cable 241 (part of a transferring means).

The computing/control circuit 240 also comprises a condition setting circuit 243 which receives signals from the decoder 242 and sets image analyzing conditions, and a memory 244 connected to the condition setting circuit 243.

When photographic conditions are input to the encoder 228 from the viewing angle setting means 236, light amount setting means 237 and switch 238 to determine whether the left or right eye is being photographed, a photographic condition data signal is output by the encoder 228. This photographic condition data signal is input to the condition setting circuit 243 via the computing/control circuit 227 and the decoder 242, and the condition setting circuit 243 stores the data in a predetermined address of the memory 244.

On the other hand, when data for identifying the left and right eyes of the subject is input to the computing-/control circuit 227 from the keyboard 239, this identifying data is input by the computing/control circuit 227 to the condition setting circuit 243 via the decoder 242. When the condition setting circuit 243 receives the identifying data, it is stored in a predetermined address of the aforesaid memory 244.

The computing/control circuit 240 comprises an image analyzing circuit 245, memory 246, frame memory 247, and control circuit 248 having a built-in CPU for controlling the circuits 243, 245 and memories 246, 247. A data inputting means 249 such as a keyboard or mouse, data read/write means 250 such as a video floppy drive unit, mini floppy drive unit or magneto-optic disk unit, and a video processing circuit 251, are connected to this control circuit 248. A monitor TV 252 is also connected to the image processing circuit 261.

When the camera switch 235 of the ophthalmological camera 201 is switched ON, this ON signal is input to the condition setting circuit 243 via the decoder 242. When the condition setting circuit 243 receives the ON signal from the camera switch 235, this ON signal is input to the control circuit 248, left/right eye identification data and photographic condition data stored in the memory 244 are recalled, and stored in a predetermined address of the memory 244 as linked data.

The control circuit 248 then drives the read/write device 250 so as to record the left/right eye identification data and photographic condition data stored in the memory 244, on a recording support or recording medium such as a floppy disk, magneto-optic disk or write once optical disk.

Further, if still image photography by the photographic device 224 is selected by the photographic mode selector switch S1 when taking the aforesaid photograph, and the control circuit 248 receives an ON signal from the camera switch 235, one frame of fundus image data transferred from the image processing circuit 225 of the ophthalmological camera 1 is stored in the frame memory 247.

At the same time, the control circuit 248 drives the read/write device 250, and records left/right eye identification data and photographic condition data stored in the memory 244 on a recording support or recording medium such as a mini-floppy disk or magneto-optic disk. Further, left/right eye identification data and the fundus image signal in the frame memory 247 are linked on the recording support. If the photograph is taken by fluorescence of the blood vessels in the fundus using angeography, a synchronizing signal is sent from the computing control circuit 227 to the control circuit 248 via a connecting cable 258 shown by a broken line when a photograph of the fundus is taken at set times. This signal is also linked to the left/right eye identification data and photographic condition data on the recording support by the frame memory 247 and control circuit 248, and is recorded on the support.

Further, when left/right eye identification data and photographic condition data are input from the inputting apparatus of the image analyzer 202, the data may also be transferred to the computing/control circuit 227 of the ophthalmological camera 1 via the connecting cable 253 shown by the broken line used in taking a photograph.

When analyzing an image with the image analyzer 202, fundus image data and photographic condition data recorded on a recording support such as a mini-floppy disk, magneto-optic disk or video floppy may be read by the read/write apparatus 250 based on indexing information for identifying the subject's eyes. In this way, the control circuit 248 and image analyzing circuit 245 may be used for analyzing, for example, the shape and size of papillae in the fundus. These analytical results are displayed on the monitor TV 252 via the image processing circuit 251.

As described hereintofore, the ophthalmological camera of this invention which obtains electronic fundus images of a subject's eyes, comprises a means for inputting photographic condition data and a data processing means for linking the fundus image obtained by the apparatus to the photographic condition data input by this inputting means. Identifying data such as left/right eye identification data for distinguishing the subject's left and right eyes, or other data, may therefore be added automatically to image data so as to relieve the nervous strain on the operator and avoid data input errors.

Further, if the aforesaid data processing means is a filing apparatus which electronically files fundus images, the aforesaid photographic condition data inputting means is an image pickup apparatus which comprises an identifying apparatus for identifying which eye has been photographed, and the aforesaid filing apparatus is set to electronically file fundus images according to the output, of the aforesaid identifying means when a photograph is taken so that the left and right eyes can be identified, this identification can be made merely by moving the chassis to the left and right on the table as is required for taking a photograph and input to the image filing apparatus. This avoids the trouble which would otherwise be caused by forgetting to specify the left or right eye, or which would be caused by confusing them.

Further, in an ophthalmological image processing system wherein the ophthalmological camera is connected to an image analyzer, and either the camera or analyzer comprises, or both comprises, a transfer means for linking photographic condition data to left/right eye identification data and transferring it to the other apparatus, input of photographic condition data to the image analyzer and ophthalmological camera is facile, and input errors can be definitively be prevented.

What is claimed is:

1. An ophthalmological image processing system comprising:
   an ophthalmological camera for electronically obtaining an ophthalmological image of a subject's eye;
   data inputting means for inputting photographic condition data; and
   data processing means for linking said ophthalmological image obtained by said ophthalmological camera to the photographic condition data input by said inputting means and processing said ophthalmological image, said data processing means including a recording means that attaches identical identification data to said ophthalmological image and said photographic condition data, and records the ophthalmological image and photographic condition data on different recording supports.

2. An ophthalmological image processing system as defined in claim 1, wherein said recording means comprises a first recording apparatus and a second recording apparatus, the first recording apparatus records the ophthalmological image together with identification data on a first recording support, and the second recording apparatus records photographic condition data together with said identification data on a second recording support.

3. An ophthalmological image processing system as defined in claim 2, wherein said first recording apparatus includes an optical recording apparatus for recording data on an optical disk, and said second recording apparatus includes a magnetic recording apparatus for recording data on a magnetic disk.

4. An ophthalmological image processing system comprising:
   an ophthalmological camera for electronically obtaining a ophthalmological image of a subject's eye;
   data inputting means for inputting photographic condition data; and
   data processing means for linking said ophthalmological image obtained by said ophthalmological camera to the photographic condition data input by said inputting means and processing said ophthalmological image, said data processing means including a recording means that attaches identical identification data to said ophthalmological image and said photographic condition data, and records the ophthalmological image and photographic condition data on the same recording support.

* * * * *